US010672158B1

(12) United States Patent
Schuck

(10) Patent No.: US 10,672,158 B1
(45) Date of Patent: Jun. 2, 2020

(54) OBJECT INTERACTIONS

(71) Applicant: TeleTracking Technologies, Inc., Pittsburgh, PA (US)

(72) Inventor: Joseph Christopher Schuck, McMurray, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 132 days.

(21) Appl. No.: 15/854,450

(22) Filed: Dec. 26, 2017

(51) Int. Cl.
*G06T 11/20* (2006.01)
*G16H 30/40* (2018.01)
*G16H 10/60* (2018.01)
*G16H 10/40* (2018.01)
*G16H 50/80* (2018.01)
*G06Q 50/26* (2012.01)
*G06Q 50/22* (2018.01)

(52) U.S. Cl.
CPC .......... *G06T 11/206* (2013.01); *G16H 10/40* (2018.01); *G16H 10/60* (2018.01); *G16H 30/40* (2018.01); *G16H 50/80* (2018.01); *G06Q 50/22* (2013.01); *G06Q 50/26* (2013.01)

(58) Field of Classification Search
CPC ...... G06T 11/206; G16H 10/10; G16H 10/60; G16H 30/40; G16H 10/40; G16H 50/80; G06Q 50/22; G06Q 50/24; G06Q 50/26
See application file for complete search history.

(56) References Cited

U.S. PATENT DOCUMENTS

| | | | |
|---|---|---|---|
| 2003/0204130 A1* | 10/2003 | Colston, Jr. | A61B 5/002 600/300 |
| 2012/0036484 A1* | 2/2012 | Zhang | H04L 41/12 715/853 |
| 2017/0024531 A1* | 1/2017 | Malaviya | G06F 19/325 |
| 2017/0352119 A1* | 12/2017 | Pittman | G06Q 50/22 |
| 2018/0067996 A1* | 3/2018 | Virshup | G06T 11/206 |

* cited by examiner

*Primary Examiner* — Ajay M Bhatia
*Assistant Examiner* — Mong-Shune Chung
(74) *Attorney, Agent, or Firm* — Ference & Associates LLC

(57) ABSTRACT

One embodiment provides a method comprising: receiving, at an input device of an information handling device, a selection to display interaction data associated with a target, wherein the interaction data corresponds to interactions between the target and at least one of an individual and an object; determining, using a processor, whether each of the interactions is associated with a direct interaction or an indirect interaction; and generating, based on the determining, an interaction visualization for the interactions. Other aspects are described and claimed.

18 Claims, 5 Drawing Sheets

OBJECT INTERACTIONS

BACKGROUND

Situations often arise in which the prior movements and activities of individuals need to be retraced and/or examined. For example, following a disease outbreak in a predetermined area (e.g., a hospital, etc.), a disease outbreak reconstructionist may desire to know the original patient or individual that carried the disease into the predetermined area, who and/or what the original patient directly interacted with, who and/or what the original patient indirectly interacted with, and the like. Information obtained from this research may help identify other individuals that may be potentially infected and/or that need to be tested for infection.

BRIEF SUMMARY

In summary, one aspect provides a method comprising: receiving, at an input device of an information handling device, a selection to display interaction data associated with a target, wherein the interaction data corresponds to interactions between the target and at least one of an individual and an object; determining, using a processor, whether each of the interactions is associated with a direct interaction or an indirect interaction; and generating, based on the determining, an interaction visualization for the interactions.

Another aspect provides an information handling device, comprising: a processor; a memory device that stores instructions executable by the processor to: receive a selection to display interaction data associated with a target, wherein the interaction data corresponds to interactions between the target and at least one of an individual and an object; determine whether each of the interactions is associated with a direct interaction or an indirect interaction; and generate, based on the determination, an interaction visualization for the interactions.

A further aspect provides a product, comprising: a storage device that stores code, the code being executable by a processor and comprising: code that receives a selection to display interaction data associated with a target, wherein the interaction data corresponds to interactions between the target and at least one of an individual and an object; code that determines whether each of the interactions is associated with a direct interaction or an indirect interaction; and code that generates, based on the code that determines, an interaction visualization for the interactions.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
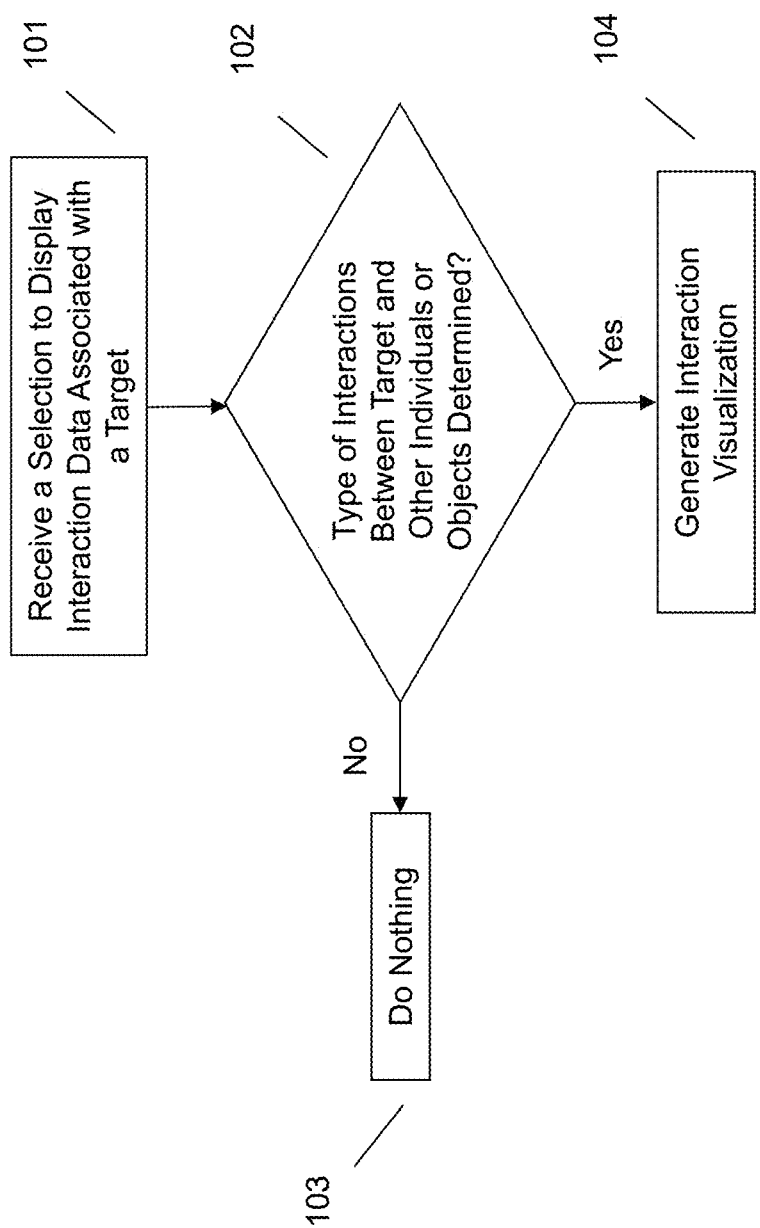
FIG. 1 illustrates an example method of generating an interaction visualization.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Reconstructing the prior movements and interactions of an individual, or a group of individuals, may be a daunting task. In some situations, records exist that describe the location a target individual was or should have been. For example, for a patient staying in a hospital, records exist that may identify which room the patient stayed in, which bed in the room the patient was assigned to, how long the patient remained in that room, and the like. Additionally, recorded information may also exist that describes who the target individual may have interacted with. For example, for a patient staying in a hospital, visitation records exist that describe who visited the patient during their stay, administrative records exist that describe which caregiver(s) (e.g., doctors, nurses, technicians, etc.) were assigned to the patient, and the like. Additionally, other types of recorded information may be accessed and examined such as video data recorded by video cameras that may provide a visual indication as to what other objects and/or people the target individual, or individuals having contacted the target individual, interacted with.

However, the aforementioned conventional records may not provide a complete picture regarding all of the interactions of a target individual. For example, individuals may enter a patient's room without having provided an official documentation of their visit or without being listed as an assigned caregiver. Additionally, these records do not record specific objects that came into contact with an individual, for example, which medical cart was used, which specific operating implement was used, or the like. Additionally, although a patient may be directed to stay in a designated area, the patient may disobey the order and wander outside the designated area. Furthermore, in the case of video cameras, certain cameras may not be always on and recording (e.g., a camera may malfunction, etc.), certain cameras may not provide an ideal view of a potential interaction (e.g., the camera is placed at a bad angle with respect to the potential interaction, etc.), or, in some situations, cameras may not be permitted to record in certain rooms and/or areas at all. The shortcomings of the conventional methods make it very difficult to create an accurate interaction visualization of a target's interactions with other individuals and/or objects. Additionally, the aforementioned conventional methods are time consuming, resource intensive, and expensive.

Accordingly, an embodiment provides a method for generating an interaction visualization that provides a user with a visualization of a target individual's interactions with other individuals and/or other objects. In an embodiment, an embodiment may receive a selection to display interaction data associated with a target. The interaction data may correspond to interactions between the target and at least one other individual or object and may be obtained using one or a multitude of tracking methodologies (e.g., Real Time Location System tracking, near field communications between objects, etc.). An embodiment may then determine whether each of the interactions is associated with a direct interaction or an indirect interaction. The rulesets that govern what constitutes a direct interaction and an indirect interaction may vary based upon a selected interaction parameter. An embodiment may then generate, based on this determination, an interaction visualization for the interactions of the target. For example, the interaction visualization may correspond to a node-and-edge graph in which the target's interactions are visually distinguished from the interactions occurring between all other individuals and/or objects in the graph. Additionally, the target's direct interactions may be visually distinguished from a target's indirect interactions. Such a method may be able to quickly provide an examining user with a comprehensive visualization of all the interactions, and interaction types, associated with a target individual. Additionally, such a method may also be used to analyze the impact of care and patient outcomes (both positive and negative) by providing insights to care team interactions, durations, equipment used, etc. Such data could enhance machine learning techniques to help healthcare providers deliver more efficacious patient care and change care protocols.

The illustrated example embodiments will be best understood by reference to the figures. The following description is intended only by way of example, and simply illustrates certain example embodiments.

Referring now to FIG. 1, an embodiment may generate an interaction visualization outlining the direct and indirect interactions between a selected target and other objects and individuals. At 101, an embodiment may receive a selection to display interaction data associated with a target. In an embodiment, interaction data may refer to data that tracks characteristics associated with any detected interaction. In an embodiment, a detected interaction may be either a direct interaction or an indirect interaction. In the context of this application, a direct interaction may be any instance in which an individual or object made contact with another individual or object (e.g., an individual touched another individual, an individual laid in a particular bed, etc.) or any instance in which an individual or object did not make contact with another individual or object but was within a predetermined distance to another individual or object (e.g., two individuals not touching but being in the same together, an individual not touching but being in the same room as an object, etc.). In the context of this application, an indirect interaction may be any instance in which an individual or object has a direct interaction with another individual or object that thereafter has a direct interaction with yet another individual or object. For example, an individual may shake hands with another individual who thereafter shakes hands with yet another individual. As another example, an individual may have sat in a chair that another individual later also sits in.

In an embodiment, the interaction data may track at least one of: the proximity of an interaction (e.g., the distance between an individual or object and another individual or object during an interaction, etc.), the length of an interaction (e.g., the duration an individual or object had an interaction with another individual or object, etc.), and the location of an interaction (e.g., which room of a hospital an interaction took place, etc.). In an embodiment, interaction data may be continuously gathered and/or received using one or more individual and/or object tracking techniques. For example, Real Time Location System (RTLS) technology may be implemented in a predetermined space (e.g., a hospital, emergency care facility, etc.) to track the location of individuals and objects to varying degrees of granularity. RTLS tags may be attached to individuals (e.g., patients, visitors, doctors, care staff, etc.) or objects (e.g., beds, chairs, etc.) to identify and record their positions as they move about the predetermined space. Through this method of tracking, it can be determined which other RTLS tagged individuals or objects a targeted individual or object had an interaction with, where the interaction occurred, and for how long the interaction occurred before. The tags may include radio frequency identification (RFID), near field, or other communication/sensing capabilities that allow the tags to communicate with each other. Alternatively, the tags may transmit location data to a system and the system may correlate the locations of objects having tags. In other words, the system determines if the tagged objects were in proximity to each other, rather than the tags communicating to each other.

In an embodiment, a target may be selected from a list of targets. As a non-limiting example, referring to FIG. 2, a user may be presented with a selection table 21 that may contain a listing of potential targets (e.g., objects or individuals, etc.) for selection (e.g., Andy, Dr. King, Francis, etc.). Upon selection of a target 22 (e.g., Patient X), the selected target 22 in the table may be visually distinguished from the unselected targets 23 (e.g., by changing a color of the selected target's box, etc.). In an embodiment, the selection of a target 22 may be made by a user providing input (e.g., touch input, stylus input, mouse input, keyboard input, verbal, image etc.) to an input device (e.g., a display screen, a hard or soft keyboard, a mouse, microphone, camera etc.) operatively coupled to the device. For example, a user may provide touch selection input to a display screen by tapping a name of a potential target in the table 21. Responsive to receiving a selection of a target 22, an embodiment may access interaction data (e.g., stored locally or remotely in an accessible storage database, etc.) associated with the target 22 (i.e., any detected interactions the target had with other individuals or objects).

Responsive to receiving a selection of a target, at 101, an embodiment may determine, at 102, whether each of the detected interactions is associated with a direct interaction or an indirect interaction. In an embodiment, the determination may be made, for example, by analyzing the tracking data. Using the aforementioned RTLS tracking methodology, a system may be able to track the positions and duration of time spent in each location for all tagged individuals and objects. Based upon this tracking information, an embodiment may identify which of the two categories a detected interaction falls into. For example, if the tracking data shows that an individual was in the same room as a target individual for a predetermined length of time (e.g., 2 milliseconds, 10 seconds, 5 minutes, etc.), an embodiment may classify this as a direct interaction. An embodiment may further classify any other individual that the individual came into proximate contact with as having an indirect interaction with the target individual. The length of time used to determine an interaction may be user configurable and can be any length of time.

In an embodiment, as part of the determination of which type of interaction a detected interaction is associated with, a user may select an interaction parameter in conjunction with selecting an interaction target. Such a selection may provide the user with information that is more tailored to their specific research interest. The interaction parameter may be a parameter that is accompanied by a predetermined ruleset that governs which interactions are direct, indirect, or not interactions at all based on the parameter. The predetermined ruleset may be set by a manufacturer/programmer or may be modified and/or created by a user. In an embodiment, an interaction parameter may be a specific illness or disease, duration of interaction, proximity of interaction, a location of interaction, and the like. In an embodiment, a combination of interaction parameters may be chosen and used.

In an example use-case of utilizing an interaction parameter, a user may select a specific disease as their interaction parameter, such as Tuberculosis, from a list (e.g., a drop-down list, etc.) containing a variety of different types of diseases/infections. The implication with this selection may be that the selected target is infected with Tuberculosis and a user may want to see the other individuals whom the target interacted with so that those other individuals may be notified and/or tested for Tuberculosis. As Tuberculosis is known to be highly contagious (i.e., through airborne transmission), the ruleset associated with the Tuberculosis interaction parameter may be more apt to classify the target's interactions as direct interactions than a disease that can only be transmitted through physical contact. For instance, using the Tuberculosis interaction parameter, another individual determined to have been in the same room as the target individual, but not touching the target individual, may still be classified as having a direct interaction with the target individual. If the user had selected a disease that is only capable of transmission through direct touching contact as the interaction parameter, then the same situation may have not resulted in an interaction classification at all because the target individual and the other individual never touched one another. In other words, the determination of a direct interaction, indirect interaction, or non-interaction may be based upon an interaction parameter.

The predetermined rulesets that govern which interactions are direct, indirect, or non-interactions may vary between interaction parameters. For example, different than the ruleset governing the Tuberculosis interaction parameter, in a duration interaction parameter, a direct interaction may correspond to a target that has interacted with an individual or object for a predetermined length of time or during a particular critical moment within a patient's stay/timeline; an indirect interaction may correspond to a target that has interacted with the individual or object for the predetermined length of time that thereafter interacts with another individual or object; and a non-interaction may correspond to a target that has not interacted with the individual or object for the predetermined length of time.

Responsive to determining that there are no interactions associated with the target, an embodiment may, at 103, take no further action. Additionally or alternatively, an embodiment may provide a visual or audible output notification to a user that no interactions have been detected (e.g., a message provided on a display screen, an audible message communicated using a speaker, etc.). Responsive to determining a type of interaction for each of the detected interactions, an embodiment may generate, at 104, an interaction visualization.

In an embodiment, the interaction visualization may provide a user with a visualization of the interactions between all individuals for which there is interaction data for. Alternatively, in another embodiment, the interaction visualization may provide a user with a visualization of the interactions for a subset of individuals (e.g., that are specified by a user, etc.). Throughout the remainder of this application, the form of the interaction visualization described and illustrated is of the form of an edge-and-node graph. However, such a form for the interaction visualization is not intended to be limiting and persons having ordinary skill in the art will recognize that the interaction visualization may take other forms, for example, data tables, acyclic graphs, and the like.

Figure 3:
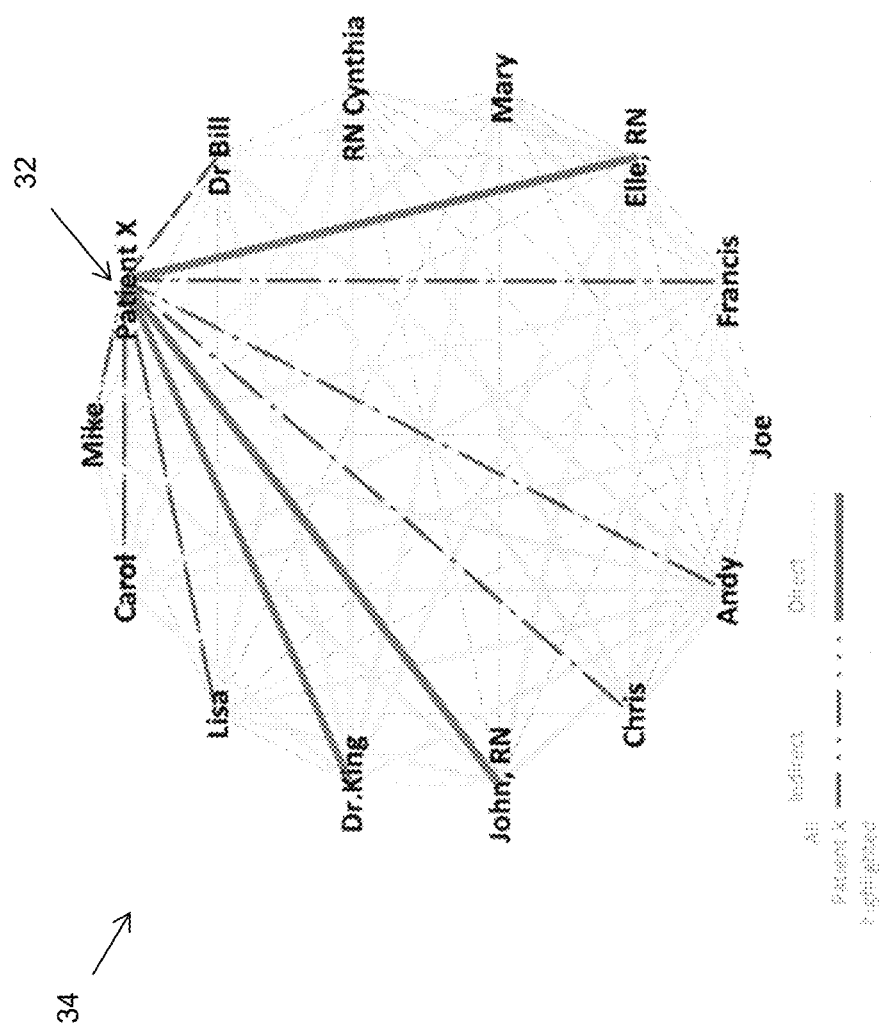
FIG. 3 illustrates an example graphical illustration of an interaction visualization according to an embodiment.

Referring now to FIG. 3, an example illustration of an edge-and-node graph 34 for a selected target 32 is illustrated. In an embodiment, each node of the graph may correspond to an individual or object and each edge of the graph may correspond to an interaction between that individual or object and another individual or object. For example, it can be seen from the graph 34 that Patient X has had interactions with Mike, Carol, Lisa, Dr. King, John, Chris, Andy, Francis, Elle, and Dr. Bill because there is an edge between Patient X and each of the aforementioned individuals. It can also be seen that there is no interaction between Patient X and Joe, Mary, and Cynthia because there is no edge between these individuals and Patient X.

In an embodiment, the interactions for a selected target 32 may be visually distinguished from the interactions between unselected targets. For example, in FIG. 3, Patient X is the selected target 32 in the graph 34 and each of Patient X's interactions may be visually distinguished from interactions in which Patient X was not involved (e.g., by graying out all interactions Patient X was not involved in, by removing all interactions Patient X was not involved in, by highlighting or changing the color of Patient X's interactions from the other interactions, etc.). In an embodiment, the direct interactions of a selected target 32 may be visually distinguished from the indirect interactions of a selected target. For example, the direct interactions in the graph 34 may be represented by solid lines and the indirect interactions in the graph 34 may be represented by broken, or dashed, lines. In this case, Patient X may have had direct interactions with Dr. King, John, and Elle and had indirect interactions with Mike, Carol, Lisa, Chris, Andy, and Francis.

The graph may also include other distinguishing features. For example, and not shown in FIG. 3, the edges may be thicker for a higher number of interactions, a longer length of interactions, or the like. As an example, if the length of the interaction between Patient X and Elle was 2 hours and the length of interaction between Patient X and John was 30 minutes, the edge between Patient X and Elle may be thicker than the edge between Patient X and John. As another example, if the number of interactions between Patient X and Dr. King was 5 and the number of interactions between Patient X and John was 15, the edge between Patient X and John may be thicker than the edge between Patient X and Dr. King. Combinations of these factors may also change the thickness of the line. For example, if the number of interactions between Patient X and Dr. King was 5 having a total duration of 3 hours, and the number of interactions between Patient X and Elle was 15 having a total duration of 30 minutes, the edge between Patient X and Dr. King may be thicker than the edge between Patient X and Elle. Other factors may be considered and other distinguishing features may be used. For example, the graph may be color coded, have different shades for different volumes of interactions, and the like.

In an embodiment, a user may attain additional interaction data regarding a specific interaction by selecting, or hovering over, a desired edge or individual. For example, if a user wanted to know specific interaction data regarding the direct interaction between Patient X and Dr. King, a user may select the edge connecting the two individuals (e.g., using touch input, mouse input, etc.). Responsive to this selection, a separate table (not pictured) may appear that may provide information indicating that Patient X and Dr. King made direct contact at a specific time (e.g., 2:30 pm on Oct. 1, 2015, etc.) in a specific place (e.g., Patient X's hospital room, etc.) and the length of that direct contact (e.g., 2 minutes, etc.).

Figure 4:
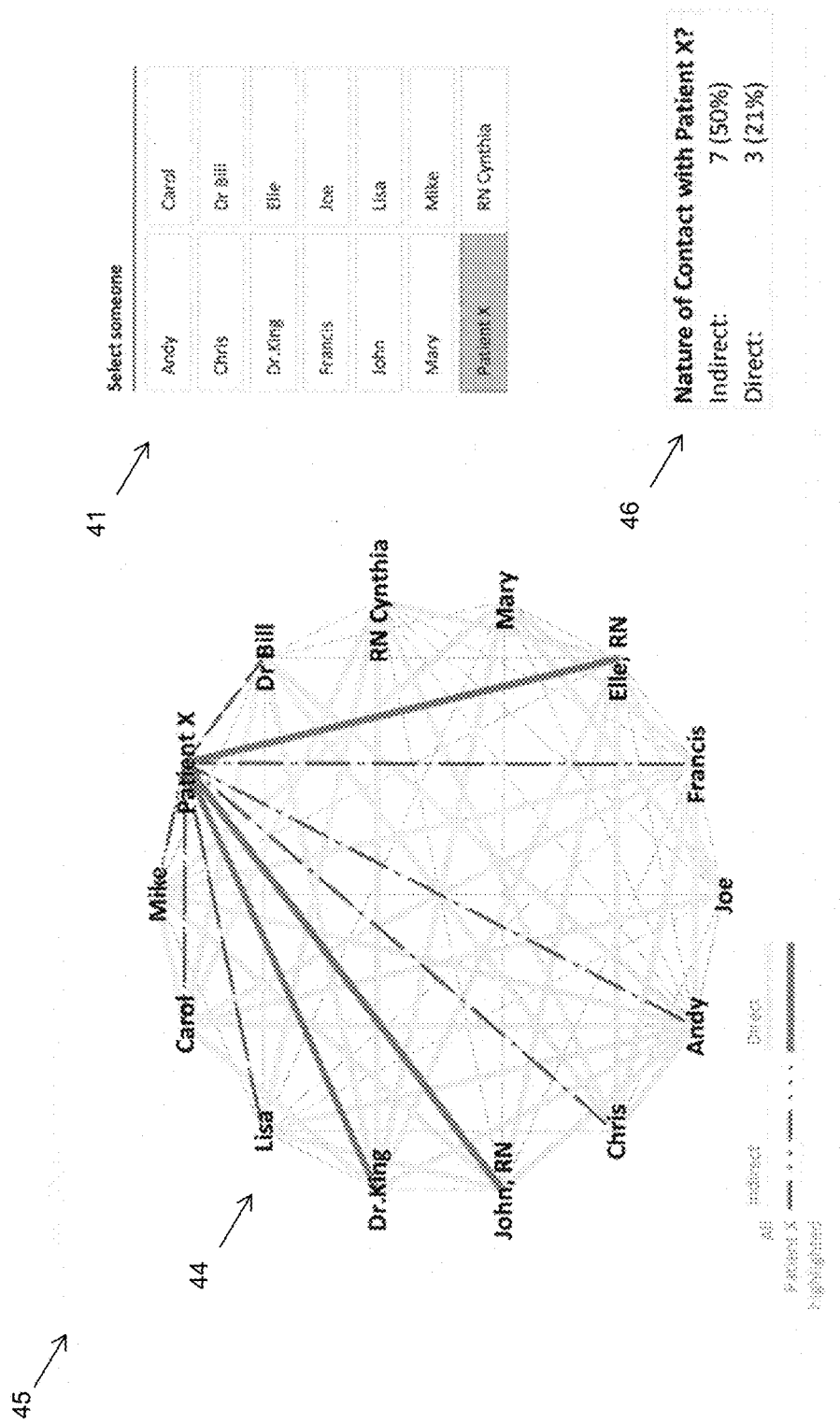
FIG. 4 illustrates another example graphical interface of an interaction visualization according to an embodiment.

In an embodiment, additional information regarding the interactions between a selected target and other individuals and/or objects may be co-displayed along with the edge-and-node graph. Referring now to FIG. 4, an example illustration of a user interface is provided in which the edge-and-node graph 44 is co-displayed along with the selection table 41, a user-adjustable time range 45 for interaction data presentation (i.e., a specific time range in which a user wishes to see interactions that occurred in that time range), and a percentage table 46 indicating the percentage of direct and indirect contacts the target had with other individuals and/or objects. Some or all of this additional information may be present in the interface. A user may choose to remove a data table by collapsing or removing an information box.

Figure 2:
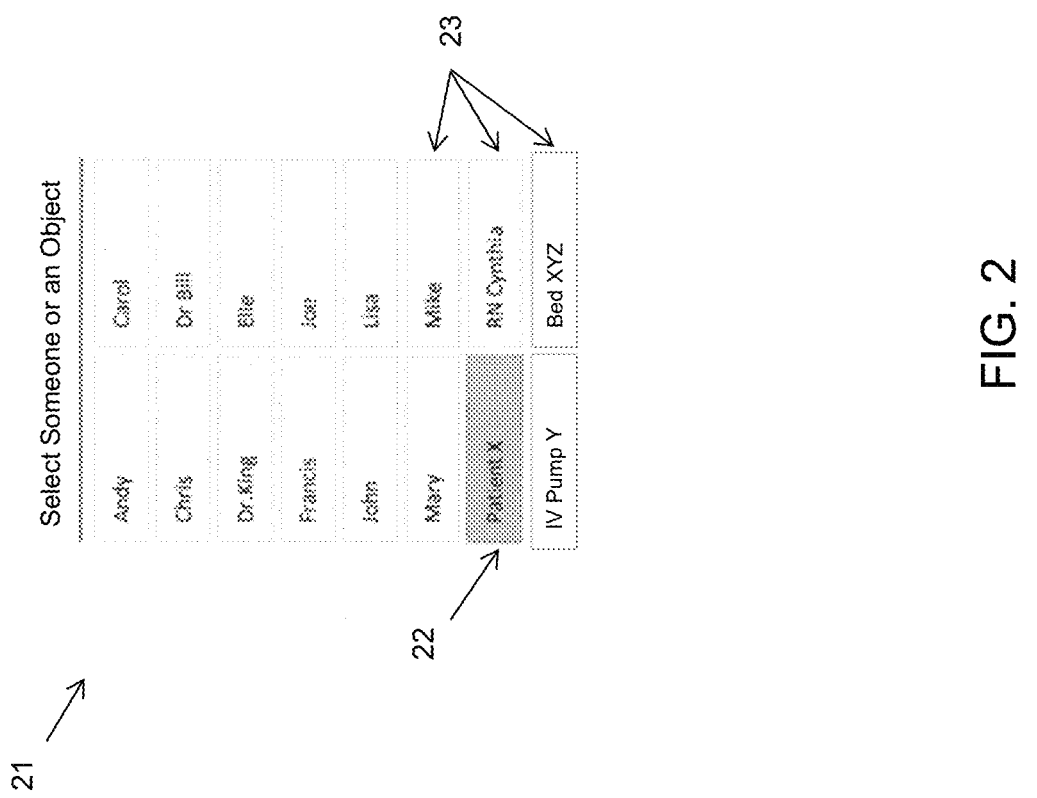
FIG. 2 illustrates an example target selection table according to an embodiment.

In an embodiment, responsive to receiving selection input for another target, the graph may dynamically update to reflect the interaction data for the newly selected target. For example, if a user were to select Francis as the new target, then the edges of the graph may dynamically update to visually distinguish all of Francis' interactions. The selection input may be received at the original selection table, for example, as shown in FIG. 2. Alternatively, the selection input may be received at the graph, for example, if a user wanted to see the interactions of Dr. King after interacting with Patient X, the user can select Dr. King from the graph of FIG. 3. In this scenario, the system may automatically apply parameters that distinguish the time frame of interactions for Dr. King. In other words, if the user selects Dr. King from the graph of FIG. 3, the system may apply a filter that only shows the interactions of Dr. King after coming into contact with Patient X.

The various embodiments described herein thus represent a technical improvement to current interaction tracking techniques. The systems and methods as described herein enable interactions between individuals and/or objects in a predetermined space to be tracked and thereafter visually displayed to a user in an interaction visualization. The interaction visualization may allow a user to quickly identify direct and indirect interactions between a targeted individual or object and another individuals or objects. Such techniques, for example, may enable users to identify origination points for a particular disease or virus and/or identify points of potential disease transmission to other individuals. Such techniques may also allow individuals to identify which individuals or objects may be in need of medical attention or sterilization.

While various other circuits, circuitry or components may be utilized in information handling devices, with a computer, server, client device or the like, an example device that may be used in implementing one or more embodiments includes a computing device in the form of a computer 500. This example device may be a server used in one of the systems in a hospital network, or one of the remote computers connected to the hospital network. Components of computer 500 may include, but are not limited to, a processing unit 520, a system memory 530, and a system bus 522 that couples various system components including the system memory 530 to the processing unit 520. Computer 500 may include or have access to a variety of computer readable media, including databases. The system memory 530 may include non-signal computer readable storage media, for example in the form of volatile and/or nonvolatile memory such as read only memory (ROM) and/or random access memory (RAM). By way of example, and not limitation, system memory 530 may also include an operating system, application programs, other program modules, and program data.

A user can interface with (for example, enter commands and information) the computer 500 through input devices 550. A monitor or other type of device can also be connected to the system bus 522 via an interface, such as an output interface 560. The computer may include a database 540, e.g., if it is part of the warehouse layer in FIG. 1. In addition to a monitor, computers may also include other peripheral output devices. The computer 500 may operate in a networked or distributed environment using logical connections to one or more other remote device(s) 580 such as other computers. The logical connections may include network interface(s) 570 to a network, such as a local area network (LAN), a wide area network (WAN), and/or a global computer network, but may also include other networks/buses.

Figure 5:
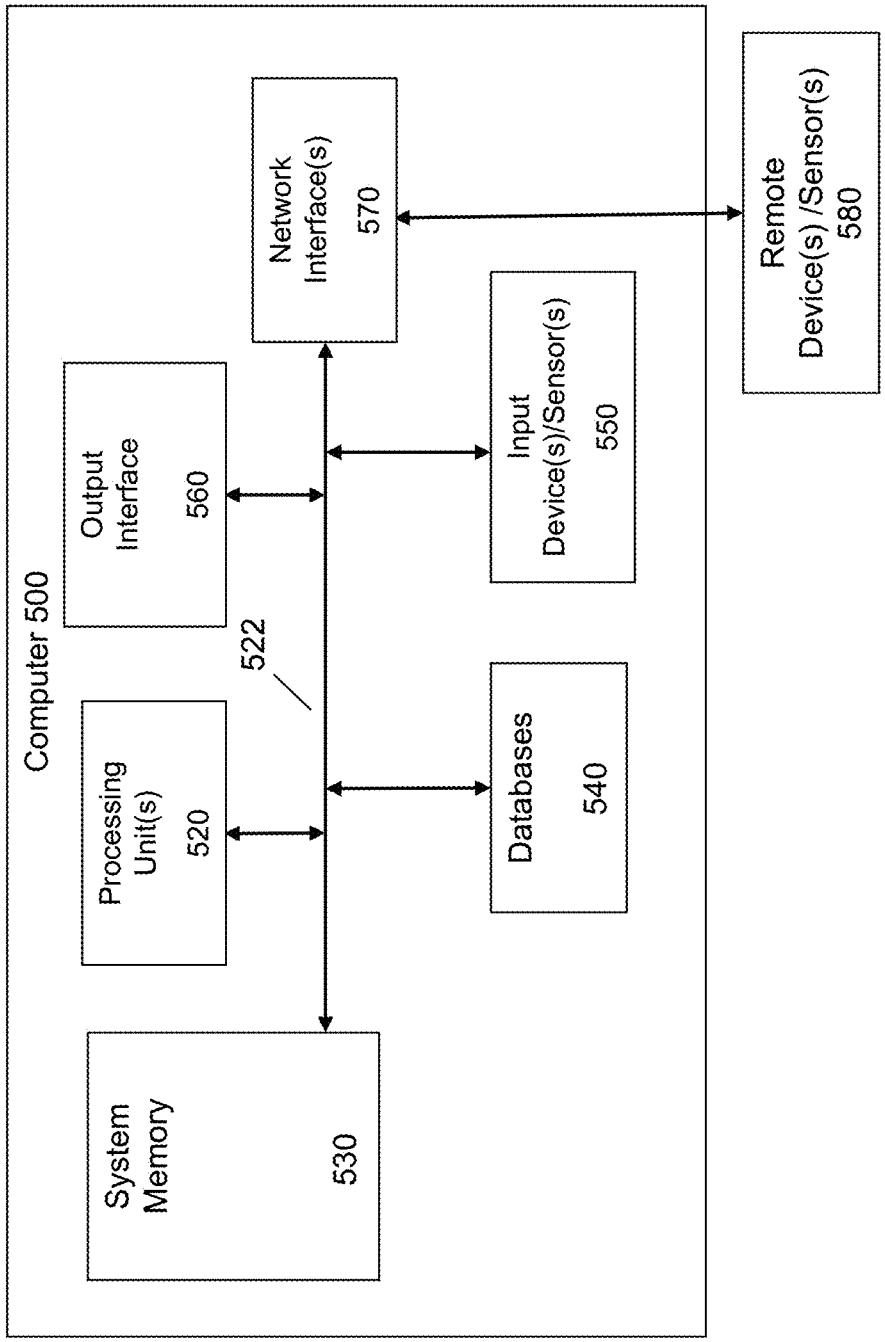
FIG. 5 illustrates an example of device circuitry/system architecture.

Information handling device circuitry, as for example outlined in FIG. 5, may be used in client devices such as a personal desktop computer, a laptop computer, or smaller devices such as a tablet or a smart phone. In the latter cases, i.e., for a tablet computer and a smart phone, the circuitry outlined in FIG. 5 may be adapted to a system on chip type circuitry. The device, irrespective of the circuitry provided, may provide and receive data to/from another device, e.g., a server or system that coordinates with various other systems. As will be appreciated by one having ordinary skill in the art, other circuitry or additional circuitry from that outlined in the example of FIG. 5 may be employed in various electronic devices that are used in whole or in part to implement the systems, methods and products of the various embodiments described herein.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device that are executed by a processor. A storage device may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method comprising:
   receiving, at an input device of an information handling device, a selection to display interaction data associated with a target, wherein the interaction data corresponds to interactions between the target and at least one of an individual and an object;
   receiving, at the information handling device, a designation of an interaction parameter, wherein the designation of the interaction parameter adjusts a defining standard for a direct interaction and an indirect interaction for the interaction data;
   determining, using a processor and based on the interaction parameter, whether each of the interactions is associated with a direct interaction or an indirect interaction; and
   generating, based on the determining, an interaction visualization for the interactions.

2. The method of claim 1, wherein the target is a human or another object.

3. The method of claim 1, wherein the target is selected by a user.

4. The method of claim 1, wherein the interaction data comprises data selected from the group consisting of at least one of interaction proximity data, interaction length data, and interaction location data.

5. The method of claim 1, wherein the interaction visualization is a graph and wherein the graph comprises a plurality of edges and a plurality of nodes, each of the plurality of edges identifying an interaction and each of the plurality of nodes identifying the individual or the object.

6. The method of claim 5, further comprising providing additional information about the interaction associated with an edge of the plurality of edges responsive to receiving selection input on the edge.

7. The method of claim 1, wherein the direct interaction is visually distinguished on the graph from the indirect interaction by at least one distinguishing aspect.

8. The method of claim 1, wherein the interaction parameter comprises a parameter selected from the group consisting of an illness, a duration of interaction, a proximity of interaction, and a location of interaction.

9. The method of claim 1, further comprising displaying interaction data associated with another target responsive to receiving another selection to display interaction data associated with the another target.

10. An information handling device, comprising:
    a processor;
    a memory device that stores instructions executable by the processor to:
    receive a selection to display interaction data associated with a target, wherein the interaction data corresponds to interactions between the target and at least one of an individual and an object;
    receive a designation of an interaction parameter, wherein the designation of the interaction parameter adjusts a defining standard for a direct interaction and an indirect interaction for the interaction data;
    determine, based on the interaction parameter, whether each of the interactions is associated with a direct interaction or an indirect interaction; and
    generate, based on the determination, an interaction visualization for the interactions.

11. The information handling device of claim 10, wherein the target is a human or another object.

12. The information handling device of claim 10, wherein the target is selected by a user.

13. The information handling device of claim 10, wherein the interaction data comprises data selected from the group consisting of at least one of interaction proximity data, interaction length data, and interaction location data.

14. The information handling device of claim 10, wherein the interaction visualization is a graph and wherein the graph comprises a plurality of edges and a plurality of nodes, each of the plurality of edges identifying an interaction and each of the plurality of nodes identifying the individual or the object.

15. The information handling device of claim 10, wherein the direct interaction is visually distinguished on the graph from the indirect interaction.

16. The information handling device of claim 10, wherein the interaction parameter comprises a parameter selected from the group consisting of an illness, a duration of interaction, a proximity of interaction, and a location of interaction.

17. The information handling device of claim 10, wherein the instructions are further executable by the processor to display interaction data associated with another target responsive to receiving another selection to display interaction data associated with the another target.

18. A product, comprising:
a storage device that stores code, the code being executable by a processor and comprising:
code that receives a selection to display interaction data associated with a target, wherein the interaction data corresponds to interactions between the target and at least one of an individual and an object;
code that receives a designation of an interaction parameter, wherein the designation of the interaction parameter adjusts a defining standard for a direct interaction and an indirect interaction for the interaction data
code that determines, based on the interaction parameter, whether each of the interactions is associated with a direct interaction or an indirect interaction; and
code that generates, based on the code that determines, an interaction visualization for the interactions.

* * * * *